United States Patent
Wang et al.

(10) Patent No.: US 9,482,630 B2
(45) Date of Patent: Nov. 1, 2016

(54) MULTIPLE-LAYERED ENERGY-INTEGRATING DETECTOR IN A HYBRID COMPUTED TOMOGRAPHY SCANNER

(71) Applicant: TOSHIBA MEDICAL SYSTEMS CORPORATION, Otawara-shi (JP)

(72) Inventors: Gin Chung Wang, Lincolnshire, IL (US); Daniel Gagnon, Twinsburg, OH (US); Michael Silver, Northbrook, IL (US); Yu Zou, Naperville, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 34 days.

(21) Appl. No.: 14/601,868

(22) Filed: Jan. 21, 2015

(65) Prior Publication Data

US 2016/0209337 A1 Jul. 21, 2016

(51) Int. Cl.
| | |
|---|---|
| *A61B 6/03* | (2006.01) |
| *A61B 6/00* | (2006.01) |
| *G01N 23/00* | (2006.01) |
| *G01N 23/04* | (2006.01) |
| *G01T 1/29* | (2006.01) |

(52) U.S. Cl.
CPC ........... *G01N 23/046* (2013.01); *G01T 1/2964* (2013.01); *G01T 1/2985* (2013.01)

(58) Field of Classification Search
USPC ............ 250/370.09, 370.1, 370.11; 378/4, 8, 378/15, 19, 21, 95, 198
See application file for complete search history.

(56) References Cited

U.S. PATENT DOCUMENTS

| | | | |
|---|---|---|---|
| 6,185,271 B1 * | 2/2001 | Kinsinger | A61B 6/032 378/19 |
| 6,553,092 B1 | 4/2003 | Mattson et al. | |
| 7,313,221 B2 * | 12/2007 | Sowerby | G01N 23/09 250/269.3 |
| 7,375,337 B2 * | 5/2008 | Gagnon | A61B 6/037 250/363.05 |
| 7,388,940 B1 * | 6/2008 | De Man | A61B 6/032 378/4 |
| 7,885,371 B2 * | 2/2011 | Thibault | G06T 11/006 378/4 |
| 8,391,439 B2 | 3/2013 | Levene et al. | |
| 8,761,333 B2 * | 6/2014 | Ikhlef | A61B 6/032 29/428 |
| 8,983,024 B2 * | 3/2015 | Zhang | A61B 6/025 378/19 |
| 2011/0200167 A1 * | 8/2011 | Naidu | G01V 5/0016 378/19 |
| 2013/0058452 A1 | 3/2013 | Levene et al. | |
| 2013/0251097 A1 | 9/2013 | Zou | |
| 2013/0292574 A1 | 11/2013 | Levene et al. | |
| 2015/0146844 A1 * | 5/2015 | Zamyatin | A61B 6/032 378/5 |
| 2016/0089071 A1 * | 3/2016 | Crawford | A61B 5/15003 600/579 |

* cited by examiner

*Primary Examiner* — Bernard Souw
(74) *Attorney, Agent, or Firm* — Oblon, McClelland, Maier & Neustadt, L.L.P.

(57) ABSTRACT

A CT scanner apparatus includes an X-ray source mounted on a gantry of the CT scanner apparatus. The CT scanner apparatus also includes a first X-ray detector mounted on the gantry opposite to the X-ray source, and configured to detect X-rays emitted from the X-ray source and transmitted through an object. The CT scanner apparatus also includes a fixed, sparse array of second X-ray detectors. Each of the second X-ray detectors includes a plurality of stacked scintillators and a photosensor adjacent to a sidewall of the stacked scintillators in a side-readout configuration.

14 Claims, 6 Drawing Sheets

MULTIPLE-LAYERED ENERGY-INTEGRATING DETECTOR IN A HYBRID COMPUTED TOMOGRAPHY SCANNER

BACKGROUND

1. Field

The exemplary embodiments described herein relate to computed tomography (CT) systems. In particular, exemplary embodiments relate to a multilayer energy-integrating detector.

2. Description of the Related Art

The X-ray beam in most computed tomography (CT) scanners is generally polychromatic. Yet, third-generation CT scanners generate images based upon data according to the energy integration nature of the detectors. These conventional detectors are called energy-integrating detectors and acquire energy integration X-ray data. On the other hand, photon-counting detectors are configured to acquire the spectral nature of the X-ray source, rather than the energy integration nature. To obtain the spectral nature of the transmitted X-ray data, the photon-counting detectors split the X-ray beam into its component energies or spectrum bins and count the number of photons in each of the bins. The use of the spectral nature of the X-ray source in CT is often referred to as spectral CT. Since spectral CT involves the detection of transmitted X-rays at two or more energy levels, spectral CT generally includes dual-energy CT by definition.

Spectral CT is advantageous over conventional CT because spectral CT offers the additional clinical information included in the full spectrum of an X-ray beam. For example, spectral CT facilitates in discriminating tissues, differentiating between tissues containing calcium and tissues containing iodine, and enhancing the detection of smaller vessels. Among other advantages, spectral CT reduces beam-hardening artifacts, and increases accuracy in CT numbers independent of the type of scanner.

Conventional attempts include the use of integrating detectors in implementing spectral CT. One attempt includes dual sources and dual integrating detectors that are placed on the gantry at a predetermined angle with respect to each other for acquiring data as the gantry rotates around a patient. Another attempt includes the combination of a single source that performs kV-switching and a single integrating detector, which is placed on the gantry for acquiring data as the gantry rotates around a patient. Yet another attempt includes a single source and dual integrating detectors that are layered on the gantry for acquiring the data as the gantry rotates around a patient. All of these attempts at spectral CT were not successful in substantially solving issues, such as beam hardening, temporal resolution, noise, poor detector response, poor energy separation, etc., for reconstructing clinically viable images.

Spectral CT also has the following short-comings. Slow kV-switching presents a problem during patient movement and when dynamic changes are made between scans. Decomposing the data domain is also very difficult. Fast kV-switching is required for high sample rates to overcome the movement problem. However, a complex and costly system is required, which still does not provide ideal waveforms, and there is a poor noise balance with spatial registration.

Dual-layer detectors have a limited energy separation and are also more costly than a single-layer detector. In addition, they are not adaptable to patient and scan conditions. Dual-source imaging systems have a problem with data domain registration, which requires the less-useful image domain spectral decomposition method, and the system is much more costly than a single-source imaging system.

Photon-counting CT systems are not ideal for general purpose, diagnostic, or clinical CT. At the high count rate required for clinical CT, pile-up and polarization present problems. The spectroscopic accuracy of the readings is questionable, due to energy sharing and K-escape. A photon-counting system is also more costly.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Embodiments herein describe a multiple-layered energy-integrating detector in a hybrid CT scanner. In some embodiments, a spectral CT apparatus includes an X-ray source and an X-ray detector configured to rotate together in a fixed perimeter about an object, and a plurality of multi-layer energy integration detectors in a stationary periphery about the object. Each of the multi-layer energy integration detectors contains multiple layered scintillators. In some embodiments, a multi-layer energy integration detector has a plurality of stacked scintillators and a plurality of alternating photosensors configured to measure spectra information from emitted X-ray photons through an object. In some embodiments, a multi-layer energy integration detector has a plurality of stacked scintillators and an adjacent photosensor configured to measure spectra information from emitted X-ray photons through an object. In some embodiments, a method of measuring spectra information from emitted X-ray photons through an object includes measuring an energy level of the emitted X-ray photons at a photosensor adjacent to a plurality of stacked scintillator materials. In some embodiments, a method of measuring spectra information from emitted X-ray photons through an object includes measuring an energy of the emitted X-ray photons through a stacked layer of alternating scintillators and respective photosensors.

In one embodiment, a CT scanner apparatus includes an X-ray source mounted on a gantry of the CT scanner apparatus. The CT scanner apparatus also includes a first X-ray detector mounted on the gantry opposite to the X-ray source, and configured to detect X-rays emitted from the X-ray source and transmitted through an object. The CT scanner apparatus also includes a fixed, sparse array of second X-ray detectors (e.g., MLIDs). Each of the second X-ray detectors includes a plurality of stacked scintillators and a photosensor adjacent to a sidewall of the stacked scintillators in a side-readout configuration.

In one embodiment, a CT scanner apparatus includes an X-ray source mounted on a gantry of the CT scanner apparatus. The CT scanner apparatus also includes a first X-ray detector mounted on the gantry opposite to the X-ray source, and configured to detect X-rays emitted from the X-ray source and transmitted through an object. The CT scanner apparatus also includes a fixed, sparse array of second X-ray detectors, each of which includes a plurality of alternating scintillators and photosensors in a layer-readout configuration.

Figure 1:
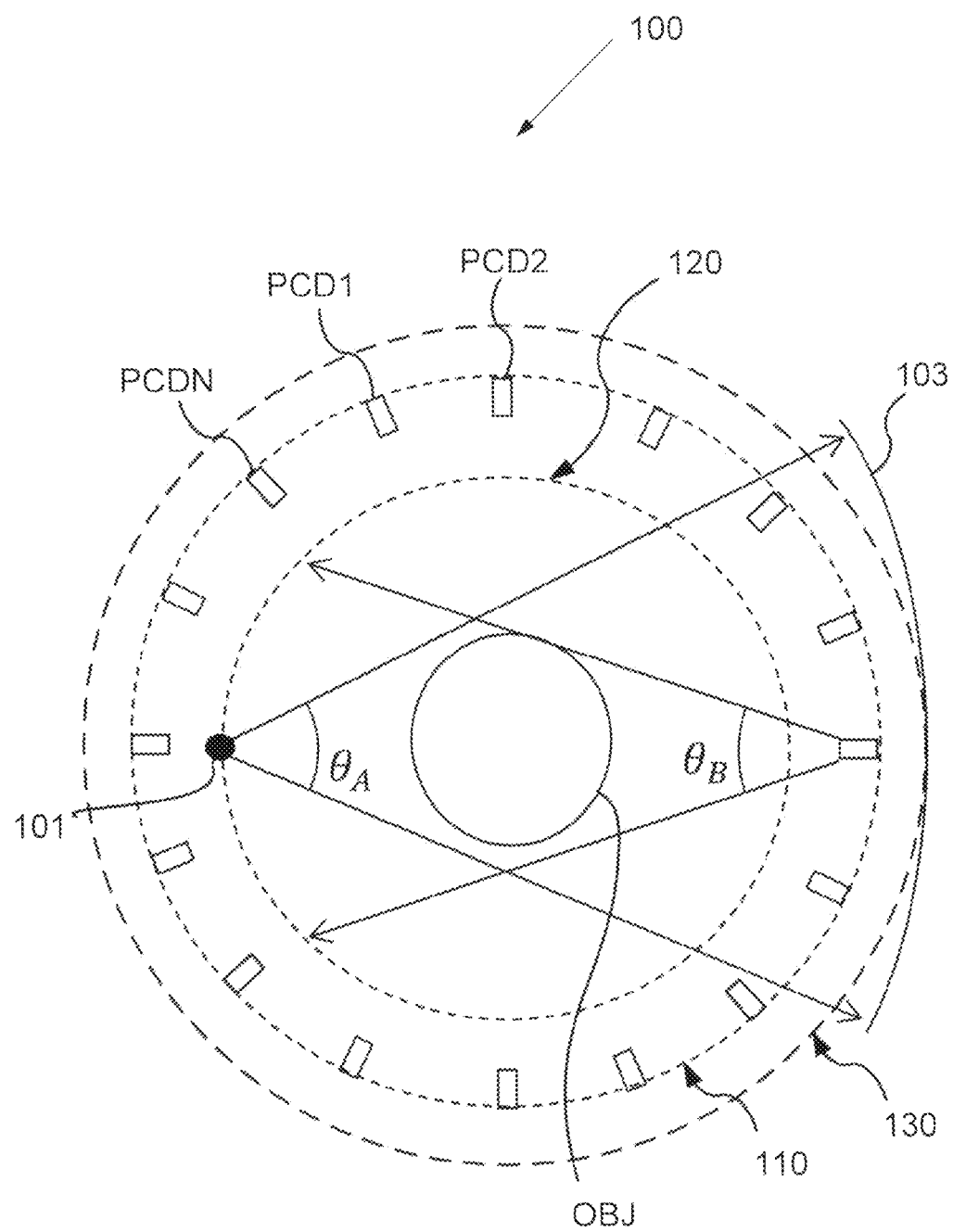
FIG. 1 is a cross-sectional diagram of a combined third-generation and fourth-generation computed tomography (CT) apparatus, according to an exemplary embodiment.

Referring now to the drawings, wherein like reference numerals designate identical or corresponding parts throughout the several views, FIG. 1 is a diagram illustrating an implementation for placing the photon-counting detectors (PCDs) having a predetermined fourth-generation geometry in combination with a detector having a predetermined third-generation geometry in a CT scanner system. The diagram illustrates relative positions among an object OBJ to be scanned, an X-ray source 101, an X-ray detector 103, and the photon-counting detectors PCD1-PCDN, in one exemplary embodiment. For the sake of simplicity, the diagram excludes other components and circuits that may be used in acquiring and processing data as well as reconstructing an image based upon the acquired data. In general, the photon-counting detectors PCD1-PCDN each output a photon count for each predetermined energy bin. In addition to the sparse photon-counting detectors PCD1-PCDN in the fourth-generation geometry, the implementation shown in FIG. 1 includes a detector, such as the detector 103, having a conventional third-generation geometry in the CT scanner system. The detector elements in the detector 103 can be more densely placed along the detector surface than the photon-counting detectors, PCD1-PCDN. See related U.S. application Ser. No. 13/426,903, the contents of which are incorporated herein by reference.

In one implementation, the photon-counting detectors PCD1-PCDN are sparsely placed around the object OBJ in a predetermined geometry such as a circle. For example, the photon-counting detectors PCD1-PCDN are fixedly placed on a predetermined circular component 110 in the gantry 100. In one implementation, the photon-counting detectors PCD1-PCDN are fixedly placed on the circular component 110 at predetermined equidistant positions. In an alternative implementation, the photon-counting detectors PCD1-PCDN are fixedly placed on the circular component 110 at predetermined non-equidistant positions. The circular component 110 remains stationary with respect to the object OBJ and does not rotate during the data acquisition.

Both the X-ray source 101 and the detector 103 rotate around the object OBJ while the photon-counting detectors PCD1-PCDN are stationary with respect to the object OBJ. In one implementation, the X-ray source 101 is mounted on a first rotating portion 120 of the annular frame in the gantry 100 so that the X-ray source 101 projects X-ray radiation with a predetermined source fan beam angle $\theta_A$ towards the object OBJ while the X-ray source 101 rotates around the object OBJ inside the sparsely placed photon-counting detectors PCD1-PCDN. Furthermore, an additional detector 103 is mounted on a second rotating portion 130 having the third-generation geometry. The rotating portion 130 mounts the detector 103 at a diametrically opposed position from the X-ray source 101 across the object OBJ and rotates outside the stationary circular component 110, on which the photon-counting detectors PCD1-PCDN are fixedly placed in a predetermined sparse manner.

In one implementation, the rotating portions 120 and 130 are integrally constructed as a single component to maintain a fixed angle (such as a 180-degree angle) between the X-ray source 101 and the detector 103 as they rotate about the object OBJ with a different radius. In an optional implementation, the rotating portions 120 and 130 are separate components, but synchronously rotate to maintain the X-ray source 101 and the detector 103 in the fixedly opposed positions at 180-degrees across the object OBJ. Furthermore, the X-ray source 101 optionally travels a helical path as the object is moved in a predetermined direction that is perpendicular to the rotational plane of the rotating portion 120.

As the X-ray source 101 and the detector 103 rotate around the object OBJ, the photon-counting detectors PCD1-PCDN and the detector 103, respectively detect the transmitted X-ray radiation during data acquisition. The photon-counting detectors PCD1-PCDN intermittently detect with a predetermined detector fan beam angle $\theta_B$ the X-ray radiation that has been transmitted through the object OBJ and each individually output a count value representing a number of photons, for each of predetermined energy bins. On the other hand, the detector elements in the detector 103 continuously detect the X-ray radiation that has been transmitted through the object OBJ and output the detected signals as the detector 103 rotates. In one implementation, the detector 103 has densely placed energy-integrating detectors in predetermined channel and segment directions on the detector surface.

In one implementation, the X-ray source 101, the photon-counting detectors PCD1-PCDN and the detector 103 collectively form three predetermined circular paths that differ in radius. The photon-counting detectors PCD1-PCDN are sparsely placed along a first circular path around the object OBJ while at least one X-ray source 101 rotates along a second circular path around the object OBJ. Further, the detector 103 travels along a third circular path. The above exemplary embodiment illustrates that the third circular path is the largest and outside the first and second circular paths around the object OBJ. Although not illustrated, an alternative embodiment optionally changes the relative relation of the first and second circular paths so that the second circular path for the X-ray source 101 is larger and outside the first circular path of the sparsely placed photon-counting detectors PCD1 through PCDN around the object OBJ. Furthermore, in another alternative embodiment, the X-ray source 101 also optionally travels on the same third circular path as the detector 103. Furthermore, the above alternative embodiments optionally provide a protective rear cover for each of the photon-counting detectors PCD1-PCDN that are irradiated from behind as the X-ray source 101 travels outside the first circular path of the sparsely placed photon-counting detectors PCD1-PCDN.

There are other alternative embodiments for placing the photon-counting detectors having a predetermined fourth-generation geometry in combination with the detector having a predetermined third-generation geometry in the CT scanner. By the same token, an additional alternative embodiment optionally includes the X-ray source 101, which is configured to or designed to perform a kV-switching function for emitting X-ray radiation at a predetermined high-level energy and at a predetermined low-level energy.

In general, the photon-counting detectors PCD1-PCDN are sparsely positioned along the circular component 110. Although the photon-counting detectors PCD1-PCDN acquire sparse view projection data, the acquired projection data is sufficient for at least dual-energy (DE) reconstruction with a sparse view reconstruction technique. In addition, the detector 103 also acquires another set of projection data, which is used to generally improve image quality. In the case that the detector 103 consists of energy-integrating detectors with anti-scatter grids, the projection data from the detector 103 is used to correct scatter on the projection data from the photon-counting detectors PCD1-PCDN. In one implementation, the integrating detectors optionally need to be calibrated in view of X-ray transmission through the predetermined circular component 110 and some of the photon-counting detectors PCD1-PCDN. In acquiring the projection data, a sampling on the source trajectory is optionally made sufficiently dense in order to enhance spatial resolution.

Figure 2:
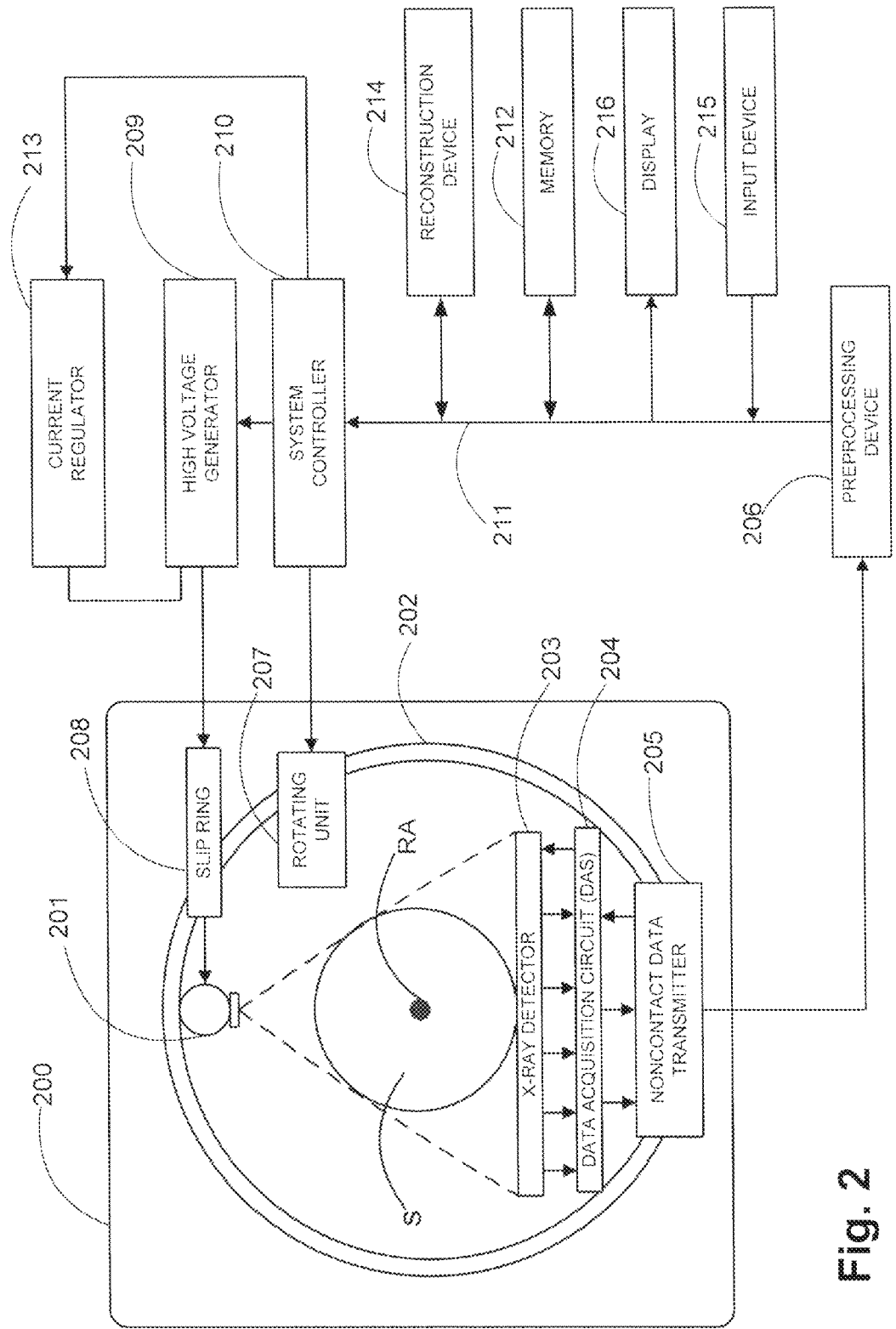
FIG. 2 illustrates an implementation of a CT system, according to an exemplary embodiment.

FIG. 2 illustrates an implementation of the radiography gantry 100 of FIG. 1 in a CT apparatus or scanner. As shown in FIG. 2, the radiography gantry 200 is illustrated from a side view and further includes an X-ray tube 201, an annular frame 202, and a multi-row or two-dimensional array type X-ray detector 203. The X-ray tube 201 and X-ray detector 203 are diametrically mounted across a subject S on the annular frame 202, which is rotatably supported around a rotation axis RA. A rotating unit 207 rotates the annular frame 202 at a high speed, such as 0.4 sec/rotation, while the subject S is being moved along the axis RA into or out of the illustrated page.

The multi-slice X-ray CT apparatus further includes a high voltage generator 209 that generates a tube voltage applied to the X-ray tube 201 through a slip ring 208 so that the X-ray tube 201 generates X-rays. The X-rays are emitted towards the subject S, whose cross sectional area is represented by a circle. The X-ray detector 203 is located at an opposite side from the X-ray tube 201 across the subject S for detecting the emitted X-rays that have transmitted through the subject S. The X-ray detector 203 further includes individual detector elements or units.

With continued reference to FIG. 2, the CT apparatus further includes other devices for processing the detected signals from X-ray detector 203. A data acquisition circuit or a Data Acquisition System (DAS) 204 converts a signal output from the X-ray detector 203 for each channel into a voltage signal, amplifies the signal, and further converts the signal into a digital signal. The X-ray detector 203 and the DAS 204 are configured to handle a predetermined total number of projections per rotation (TPPR). Examples of TPPRs include, but are not limited to 900 TPPR, 900-1800 TPPR, and 900-3600 TPPR.

The above-described data is sent to a preprocessing device 206, which is housed in a console outside the radiography gantry 200 through a non-contact data transmitter 205. The preprocessing device 206 performs certain corrections, such as sensitivity correction on the raw data. A memory 212 stores the resultant data, which is also called projection data at a stage immediately before reconstruction processing. The memory 212 is connected to a system controller 210 through a data/control bus 211, together with a reconstruction device 214, input device 215, and display 216.

The detectors are rotated and/or fixed with respect to the patient among various generations of the CT scanner systems. The above-described CT system is an example of a combined third-generation geometry and fourth-generation geometry system. In the third-generation system, the X-ray tube 201 and the X-ray detector 203 are diametrically mounted on the annular frame 202 and are rotated around the subject S as the annular frame 202 is rotated about the rotation axis RA. In the fourth-generation geometry system, the detectors are fixedly placed around the patient and an X-ray tube rotates around the patient.

In an alternative embodiment, the radiography gantry 200 has multiple detectors arranged on the annular frame 202, which is supported by a C-arm and a stand.

FIG. 1 illustrates an implementation for placing photon-counting detectors (PCDs) in a predetermined fourth-generation geometry in combination with a detector in a predetermined third-generation geometry in a CT scanner system. In general, PCDs each output a photon count for each of predetermined energy bins. The PCDs acquire sparse-view projection data for reconstruction using a sparse-view reconstruction technique.

One embodiment alters this implementation by substituting multiple-layered energy-integrating detectors in lieu of the PCDs in the predetermined fourth-generation geometry. Energy-integrating detectors output a single integration value for all of the energy components. Energy-integrating detectors acquire a second set of projection data, which is used to generally improve image quality.

An alternative embodiment to the PCD arrangement illustrated in FIG. 1, with the substituted multiple-layered energy-integrating detectors described above will now be described. The PCDs in a fixed-sparse PCD arrangement, as illustrated in FIG. 1 are replaced with multiple-layered energy-integrating detectors to measure spectral information of a received photon from an X-ray source.

Figure 3:
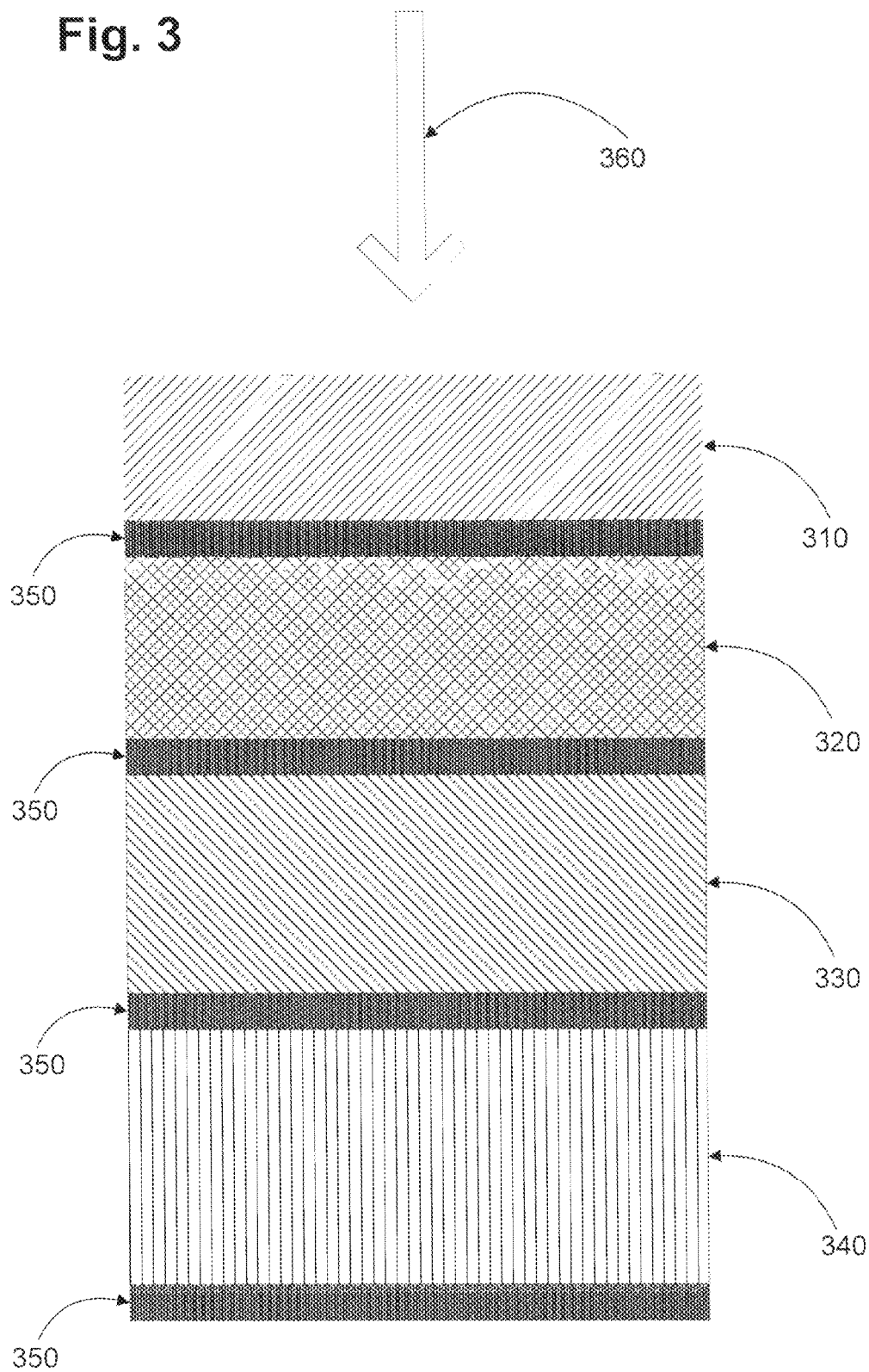
FIG. 3 is an illustration of a multiple-layered energy-integrating detector (MLID) in a layer readout configuration (L-MLID), according to an exemplary embodiment.

FIG. 3 illustrates a multiple-layered energy-integrating detector in a layer readout configuration (L-MLID). The L-MLID contains a scintillator-A 310, a scintillator-B 320, a scintillator-C 330, and a scintillator-D 340. Each of the scintillators has an optically coupled photosensor 350 located on the bottom surface of the scintillator. The alternating scintillators and photosensors are arranged in a stacked layer configuration. The scintillator-A 310, scintillator-B 320, scintillator-C 330, and scintillator-D 340 can all be of a different material type, they can all have the same material type, or they can be a combination of some having the same material type and others having a different material type.

FIG. 3 illustrates four scintillators. However, less than four or more than four scintillators are contemplated by embodiments described herein, wherein each scintillator layer has an associated photosensor layer 350. In addition, each of the scintillators can have the same material thickness or a different material thickness. A photon 360 is emitted from an X-ray source and transmitted through an object (such as a patient), and is received by the L-MLID in the direction illustrated.

When designing a configuration of multiple-stacked photon detectors, the thickness of each detector should be set such that a proper ratio of interaction between the detectors is obtained. Thus, the detector layer closer to the entrance plane of the radiation should be thinner than a deeper detector layer in order to capture the same or nearly the same amount of photons. In addition, an effective spectrum of energy levels needs to be in place for a broad energy beam or flux. Also, photons from a lower energy portion of the spectrum are preferably detected in the first detector(s) of radiation penetration, and photons with more energy are detected in the deeper detector(s).

Figure 4:
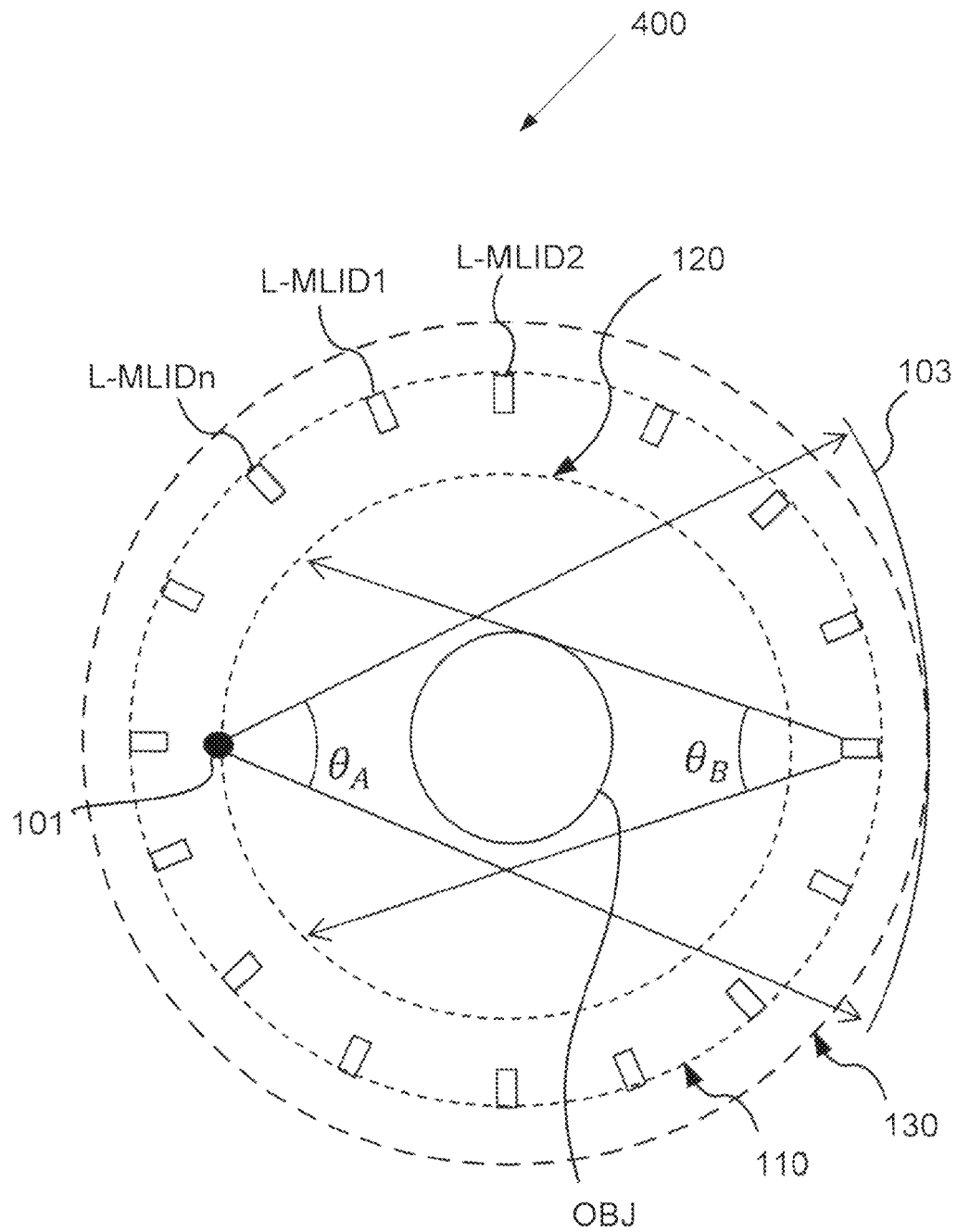
FIG. 4 is a cross-sectional diagram of a third-generation CT apparatus combined with a plurality of L-MLIDs in a fourth generation CT apparatus, according to an exemplary embodiment.

FIG. 4 illustrates a hybrid CT scanner 400, in which the PCDs of FIG. 1 have been replaced with L-MLIDs. The L-MLIDs are sparsely situated around a circumference 110 which remains stationary, while the X-ray source 101 and the X-ray detector 103 rotate together about the circumference 120 and the circumference 130, respectively. However, other configurations are contemplated by embodiments described herein, such as a rotating L-MLID circumference 110 and/or a stationary X-ray detector circumference 130. In addition, each circumference 110, 120, and 130 can have a circular gantry rotation or a helical gantry rotation.

One method to encode the energy of a detected photon is to measure the effect of the interaction of the photon in a material in an active energy discrimination process. A direct or an indirect class of detector can be used. In an indirect detector, the photon interaction will create light that is measured with a light sensor. In a direct-conversion detector, the photon directly creates a charge in the material, which is collected and fed to a specifically designed electrical circuit.

Another method of obtaining energy information is through a passive energy discrimination process. Interaction of photons with matter is stochastic in nature, and parameters of the interaction depend on the energy of the photon and the nature of the material, such as its electron density and effective atomic number. A configuration of two or more stacked detectors can extract information on the interactions of the photons at each detector in the stack. A stacked configuration of photon detectors provides a depth of interaction of X-ray photons, which is energy-dependent.

Each of the scintillator-A 310, scintillator-B 320, scintillator-C 330, and scintillator-D 340, illustrated in FIG. 3 contains a direct-conversion material. The scintillator material is chosen to generate a signal in response to impingement of incoming X-rays from the X-ray source 101. The generated signal is detected by circuitry in the optically-coupled photosensor layer 350 to generate an electrical voltage or current output signal. The multiple photosensor layers 350 are interconnected for each L-MLID to provide a single electrical output channel. Examples of a photosensor include, but are not limited to a photodiode and a silicon photomultiplier (SiPM). The scintillator layers, scintillator-A 310, scintillator-B 320, scintillator-C 330, and scintillator-D 340 are designed and configured to capture a wide spectrum of energy from the incoming X-rays. Further, the stacked scintillator layers include a broad range of materials from a low-density material with a low-Z value to a high-density material with a high Z-value. The scintillator thickness can also be varied to further define a particular range of X-ray energies to be captured at each scintillator layer.

Figure 5:
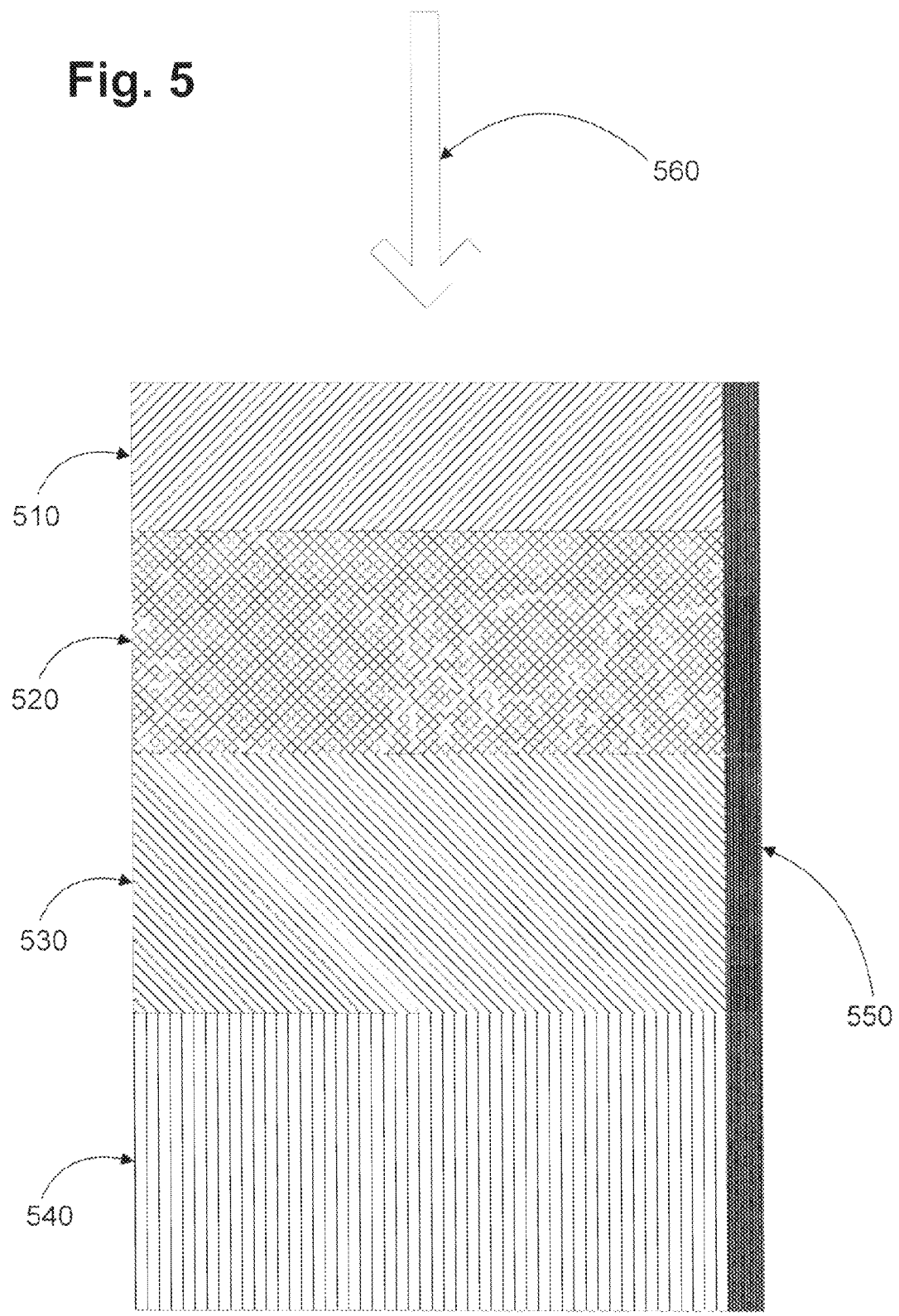
FIG. 5 is an illustration of a MLID in a side readout configuration (S-MLID), according to an exemplary embodiment.

FIG. 5 illustrates one embodiment for a multiple-layered, energy-integrating detector in a side readout configuration (S-MLID). The S-MLID contains a scintillator-A 510, a scintillator-B 520, a scintillator-C 530, and a scintillator-D 540 in a stacked configuration. FIG. 5 illustrates four scintillator layers. However, fewer than four or more than four scintillator layers are contemplated by embodiments described herein. The scintillator layers can comprise the same material or different materials and can have multiple thicknesses in order to capture a specific range of photon energies at each scintillator layer. A photon 560 is emitted from an X-ray source and is transmitted through an object and is received by the S-MLID in the direction illustrated. A photosensor layer 550 is arranged along the sides of the stacked scintillator layers.

Figure 6:
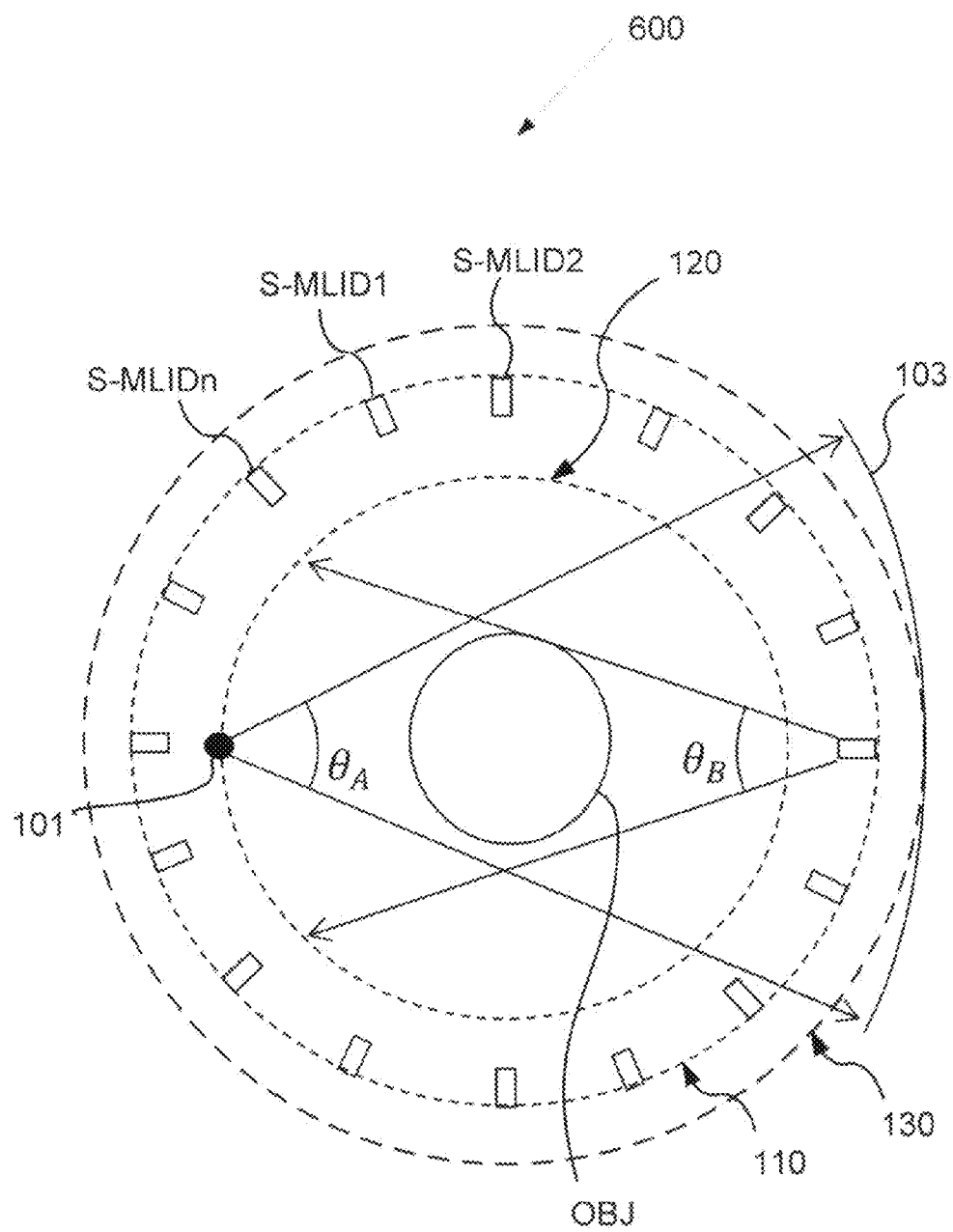
FIG. 6 is a cross-sectional diagram of a third-generation CT apparatus combined with a plurality of S-MLIDs in a fourth generation CT apparatus, according to an exemplary embodiment.

FIG. 6 illustrates a hybrid CT scanner 600, in which the PCDs of FIG. 1 have been replaced with S-MLIDs. The S-MLIDs are sparsely situated around a circumference 110 which remains stationary, while the X-ray source 101 and the X-ray detector 103 rotate together about the circumference 120 and the circumference 130, respectively. However, other configurations are contemplated by embodiments described herein, such as a rotating S-MLID circumference 110 and/or a stationary X-ray detector circumference 130. In addition, each circumference 110, 120, and 130 can have a circular gantry rotation or a helical gantry rotation.

One advantage of the sparsely-spaced S-MLIDs is having adequate space for the side-projecting photosensor of the stacked multiple-layered scintillators. The side read-out configuration of the photosensor circuitry is provided with ample space between the sparsely-spaced S-MLIDs.

Another advantage of embodiments described herein includes having more information from spectrometric measurements of the multiple-stacked detectors in a nominal mode than a single layer of the same or similar detector. The multiple-stacked detector system has statistical samples from several realizations of the incoming radiation beam.

Another advantage of multiple-stacked photon detectors is the ability to use a very thin electrode with essentially no effect on the incoming photon beam. In addition, if the first detector is silicon-based, a lower density in a z-axis direction offers a preferential detection of a lower energy of the energy spectrum, which offers a wider range of thicknesses for overall optimization.

In one embodiment, a first group of photons is received at a first scintillator, which is stack upon a first photosensor. A second group of photons is received at a second scintillator, which is stacked upon a second photosensor. This alternation of scintillators and photosensors is stacked in a layer readout configuration. In another embodiment, a first group of photons is received at a first scintillator, which is stacked upon a second scintillator. A second group of photons is received at the second scintillator. The first group of photons and the second group of photons are detected, via an associated photosensor, where the associated photosensor is adjacent to a sidewall of the stacked first and second scintillators in a side readout configuration.

Further, in an alternative embodiment, the first (rotating) X-ray detector is omitted, and scanning is performed with the rotating X-ray source and the plurality of fixed MILDs. In another alternative embodiment, the first (rotating) X-ray detector is omitted and the MILDs are arranged in a third-generation geometry and rotate in synchronization with the X-ray source.

While certain implementations have been described, these implementations have been presented by way of example only, and are not intended to limit the scope of the disclosure. The novel devices, systems, and methods described herein may be embodied in a variety of other forms. Furthermore, various omissions, substitutions, and changes in the form of the devices, systems, and methods described herein may be made without departing from the spirit of the disclosures. The accompanying claims are intended to cover such forms or modifications as would fall within the scope and spirit of the disclosures.

The invention claimed is:

1. A computed tomography (CT) scanner apparatus, comprising:
   an X-ray source mounted on a gantry of the CT scanner apparatus;
   a first X-ray detector mounted on the gantry opposite to the X-ray source, and configured to detect X-rays emitted from the X-ray source and transmitted through an object; and a fixed, sparse array of second X-ray detectors, wherein each of the second X-ray detectors includes a plurality of stacked scintillators and a photosensor circuit adjacent to a sidewall of the stacked scintillators in a side-readout configuration.

2. The CT scanner apparatus of claim 1, wherein the photosensor circuit includes a plurality of interconnected photosensors, one for each of the plurality of stacked scintillators.

3. The CT scanner apparatus of claim 1, wherein the photosensor circuit includes a silicon photomultiplier.

4. The CT scanner apparatus of claim 1, wherein the X-ray source and the first X-ray detector are configured to rotate together about the object.

5. The CT scanner apparatus of claim 1, wherein each of the plurality of scintillators includes a material that is different from the other scintillators.

6. The CT scanner apparatus of claim 1, wherein each of the plurality of scintillators includes a same material.

7. The CT scanner apparatus of claim 1, wherein each of the plurality of scintillators has a material thickness that is different from other scintillators of the plurality of scintillators.

8. The CT scanner apparatus of claim 1, wherein the second X-ray detectors are mounted on the gantry.

9. A computed tomography (CT) scanner apparatus, comprising:

an X-ray source mounted on a gantry of the CT scanner apparatus;

a first X-ray detector mounted on the gantry opposite to the X-ray source, and configured to detect X-rays emitted from the X-ray source and transmitted through an object; and a fixed, sparse array of second X-ray detectors, wherein each of the second X-ray detectors includes a plurality of alternating scintillators and photosensors in a layer-readout configuration.

10. The CT scanner apparatus of claim 9, wherein the X-ray source and the first X-ray detector are configured to rotate together about the object.

11. The CT scanner apparatus of claim 9, wherein each of the plurality of scintillators includes a material that is different from other scintillators of the plurality of scintillators.

12. The CT scanner apparatus of claim 9, wherein each of the plurality of scintillators includes a same material.

13. The CT scanner apparatus of claim 9, wherein each of the plurality of scintillators has a material thickness that is different from other scintillators of the plurality of scintillators.

14. The CT scanner apparatus of claim 9, wherein the second X-ray detectors are mounted on the gantry.

* * * * *